United States Patent
Riondel et al.

(10) Patent No.: US 9,403,750 B2
(45) Date of Patent: Aug. 2, 2016

(54) METHOD FOR PRODUCING 2-OCTYL ACRYLATE BY DIRECT ESTERIFICATION

(71) Applicant: Arkema France, Colombes (FR)

(72) Inventors: Alain Riondel, Forbach (FR); Coralie Graire, Grezieu-la-Varenne (FR); Andre Levray, Procelette (FR); Reinhard Linemann, Saarbrucken (DE)

(73) Assignee: Arkema France, Colombes (FR)

(*) Notice: Subject to any disclaimer, the term of this patent is extended or adjusted under 35 U.S.C. 154(b) by 0 days.

(21) Appl. No.: 14/354,986

(22) PCT Filed: Oct. 30, 2012

(86) PCT No.: PCT/FR2012/052502
§ 371 (c)(1),
(2) Date: Apr. 29, 2014

(87) PCT Pub. No.: WO2013/064775
PCT Pub. Date: May 10, 2013

(65) Prior Publication Data
US 2015/0299093 A1    Oct. 22, 2015

(30) Foreign Application Priority Data

Nov. 4, 2011 (FR) ..................................... 11 59983
Jul. 5, 2012 (FR) ..................................... 12 56457

(51) Int. Cl.
C07C 67/08 (2006.01)
C07C 67/54 (2006.01)
C07C 67/58 (2006.01)

(52) U.S. Cl.
CPC .................. *C07C 67/08* (2013.01); *C07C 67/54* (2013.01); *C07C 67/58* (2013.01); *Y02P 20/584* (2015.11)

(58) Field of Classification Search
CPC ........ C07C 67/08; C07C 69/54; C07C 67/58; C07C 67/54; Y02P 20/584
USPC .......................................................... 560/214
See application file for complete search history.

(56) References Cited

U.S. PATENT DOCUMENTS

| | | | |
|---|---|---|---|
| 6,072,076 A * | 6/2000 | Schmidt .................. | C07C 67/08 560/205 |
| 6,084,122 A | 7/2000 | Garza, Jr. et al. | |
| 6,084,128 A | 7/2000 | Warner et al. | |
| 6,617,470 B1 * | 9/2003 | Aichinger ............... | C07C 67/08 560/205 |
| 2008/0015384 A1 * | 1/2008 | Haramaki ............... | C07C 67/08 560/129 |
| 2008/0087196 A1 | 4/2008 | Anderson et al. | |

FOREIGN PATENT DOCUMENTS

CN    1 298 863    6/2001

OTHER PUBLICATIONS

Ohara ("Acrylic Acid and Derivatives" Ullmann's Encyclopedia of Industrial Chemistry, Published Online : Oct. 15, 2011, DOI: 10.1002/14356007.a01_161.pub3, p. 1-18).*

* cited by examiner

*Primary Examiner* — Jafar Parsa
*Assistant Examiner* — Amy C Bonaparte
(74) *Attorney, Agent, or Firm* — Lynn B. Morreale (57) ABSTRACT

The invention relates to a process for continuously producing 2-octyl acrylate by reacting acrylic acid and 2-octanol in the presence of a sulfonic acid esterification catalyst and at least one polymerization inhibitor. The water formed by the esterification reaction is entrained by distillation in a column surmounting the reactor in the form of a heteroazeotropic mixture with the 2-octanol which is then subjected, after condensation, to separation in a decanter so as to give an upper organic phase and a lower aqueous phase. The reaction mixture containing the reaction product and residual by-products are purified by separation means in order to obtain: (1) pure 2-octyl acrylate and (2) unreacted 2-octanol and acrylic acid compounds that will be recycled along with the catalyst.

9 Claims, 3 Drawing Sheets

METHOD FOR PRODUCING 2-OCTYL ACRYLATE BY DIRECT ESTERIFICATION

CROSS-REFERENCE TO RELATED APPLICATIONS

This application is a national stage application under 35 U.S.C. §371 of PCT/FR2012/052502, filed Oct. 30, 2012, which claims benefit to French patent application FR 11.59983, filed on Nov. 4, 2011 and to French patent application FR 12.56457, filed Jul. 5, 2012.

FIELD OF THE INVENTION

The present invention relates to the production of 2-octyl acrylate according to a continuous process by direct esterification.

TECHNICAL BACKGROUND

It is known practice to produce acrylic esters by carrying out an esterification reaction between an alcohol and acrylic acid. This reaction is an equilibrated catalyzed reaction with generation of water:

It is necessary to remove the water produced during the reaction in order to shift the equilibrium in the direction of the production of the acrylic ester.

This reaction is generally accompanied by side reactions which produce impurities that it is necessary to remove with a view to obtaining the acrylic ester with a high purity which meets the technical requirements associated with its final use as a monomer for manufacturing polymers that can be used in numerous fields of application.

Moreover, for obvious economic reasons, the exploitable products present in the crude reaction mixture, in particular the unreacted reagents and the catalyst, are as far as possible recycled within the process.

To these ends, a separation/purification process comprising a set of distillations, extractions and/or separations by settling out, which is both relatively complex to carry out, in particular due to the presence of azeotropic mixtures, and costly in terms of energy, is generally carried out.

Document U.S. Pat. No. 6,072,076 describes a process for producing alkyl(meth)acrylates by esterification of (meth)acrylic acid with an alcohol which has a chain length ranging from 1 to 8 carbon atoms, in the presence of an acid catalyst. In this process, the equilibrium of the reaction is shifted by removal of a mixture comprising water and alcohol in a rectification unit III at the top of the reaction zone. The aqueous mixture, after condensation, is treated in a separator 17 in order to purify the alcohol and recycle it to the reaction by means of the rectification column III, the separated aqueous phase being partially returned to the rectification unit III.

In this process, the reaction mixture resulting from the reaction zone is sent to a rectification unit I in which the mixture is separated into a product (I) comprising the desired ester, the residual alcohol and the residual acid, and a product (II) comprising the catalyst; the product (I) is subjected to a second rectification unit II in which the desired ester is separated from the residual alcohol and acid products, which are recycled to the reaction zone, the purified ester being taken off at the side.

This process is illustrated with the manufacture of 2-ethylhexyl acrylate from the alcohol 2-ethylhexanol, carried out by means of two reactors 5 and 6 placed in series and operating at different heat levels. The rectification column III, the liquid reflux 13 of which contains partially recycled water, surmounts the first reactor. A crude reaction mixture containing 70% of 2-ethylhexyl acrylate is derived from this first reactor 5. The reaction is continued in the second reactor 6 with continuous take-off of the water produced by the reaction using the rectification unit III so as to achieve a final 2-ethylhexyl acrylate content of 82%.

In the process described in document U.S. Pat. No. 6,072,076, because of the introduction of recycled water into the rectification column, the removal of the water generated by the reaction is not complete for shifting the equilibrium of the reaction. It therefore proves to be necessary to use a second reactor in order to achieve satisfactory yields.

The process described in document U.S. Pat. No. 6,072,076 is not applicable to the manufacture of 2-octyl acrylate via an esterification reaction of acrylic acid and of 2-octanol. This is because 2-octanol is a secondary alcohol which is much more sensitive than a primary alcohol, such as 2-ethylhexanol, to a dehydration reaction in the presence of acid catalyst, leading to the formation of octenes and of water. There is a risk that this formation of water, accumulated with the reintroduction into the system of at least one part of the aqueous phase generated by the esterification reaction, will more readily retrograde the desired 2-octyl acrylate to 2-octanol and acrylic acid by hydrolysis. Moreover, according to said document, the purification of the crude reaction mixture comprising the desired acrylate and residual alcohol is carried out by distillation in the rectification unit I with a long residence time in the presence of the acid catalyst. In the case of a synthesis with 2-octanol, there is also a risk that this distillation will generate octenes and water and will at least partially degrade the 2-octyle acrylate formed.

The Applicant Company has sought to solve these various problems associated with the use of 2-octanol in the esterification reaction with acrylic acid.

In document US 2008/0087196, the synthesis of 2-octyl acrylate according to an esterification reaction with 2-octanol, in the presence of p-toluenesulfonic acid, is described. The reaction is carried out in a solvent medium in order to remove the water produced in the form of a toluene/water azeotrope. Such a process is nevertheless complicated to implement on an industrial scale.

Moreover, documents EP 1 027 322 and EP 1 028 936 describe a process for removing the sulfur originating from the use of a sulfonic acid catalyst, in a process for the production of acrylate, in particular of butyl acrylate, of 2-ethylhexyl acrylate or of polyol acrylate. However, the application of such a process for the synthesis of 2-octyl acrylate is in no way suggested.

There still remains therefore a need to have a process for manufacturing 2-octyl acrylate which has a productivity compatible with industrial-scale manufacture and which results in a 2-octyl acrylate which meets the purity requirements associated with its final use.

The objective of the present invention is the manufacture of a 2-octyl acrylate of very high purity with a high yield with the use of a single reactor, and including the recycling of the exploitable products such as, on the one hand, the unreacted reagents and, on the other hand, the acid catalyst, in particular an acid catalyst comprising sulfur, in particular of the sulfonic acid type.

The solution proposed consists in not directly reintroducing the aqueous phase produced by the reaction into the rectification column in order to optimize the shift in equilibrium of the reaction in the direction of the production of the ester, and in separating the acid catalyst with a view to the recycling thereof prior to the whole of the process for purifying the desired 2-octyl acrylate.

According to the invention, the catalyst, in particular acid catalyst comprising sulfur, is reused in the reaction process. The emission of organosulfur compounds during the process for producing 2-octyl acrylate using a catalyst of sulfonic acid type is thus reduced, making the process according to the invention environmentally friendly.

The present invention also makes it possible to produce an acrylic ester comprising carbon of renewable origin associated with the use of 2-octanol, which is an alcohol derived from vegetable matter.

SUMMARY OF THE INVENTION

A subject of the present invention is therefore a process for continuously producing 2-octyl acrylate by reaction of acrylic acid and of 2-octanol in the presence of an esterification catalyst of acid type comprising sulfur and of at least one polymerization inhibitor, the water formed by the esterification reaction being entrained by distillation in a column surmounting the reactor in the form of a heteroazeotropic mixture with the 2-octanol which is then subjected, after condensation, to a separation in a decanter so as to give an upper organic phase and a lower aqueous phase, the reaction mixture containing the reaction product and residual by-products being subjected to a purification treatment by separation means, in order to obtain, on the one hand, pure 2-octyl acrylate, on the other hand, the unreacted 2-octanol and acrylic acid compounds intended to be recycled, and also the catalyst intended to be recycled, said process being characterized in that:
- the aqueous phase derived from the decanter is continuously taken off so as to be removed;
- the organic phase derived from the decanter is continuously recycled at the bottom of the distillation column surmounting the reactor;
- the treatment for purification of the reaction mixture comprises (i) the separation of a catalyst-rich stream which is at least partly recycled to the reaction step, (ii) the separation of a stream rich in unreacted 2-octanol which is at least partly recycled to the reaction step, and (iii) the recovery of the desired pure 2-octyl acrylate.

The expression "rich" used in the definition of the invention is employed in a relative sense, in order to distinguish the streams from one another. Thus, the "stream rich in 2-octyl acrylate" is a stream comprising more 2-octyl acrylate than the "stream rich in 2-octanol" and than the "stream rich in catalyst and polymerization inhibitor"; the "stream rich in 2-octanol" is a stream comprising more 2-octanol compound than the "stream rich in 2-octyl acrylate".

According to the invention, the reaction mixture contains the reaction product (2-octyl acrylate) and residual by-products (heavy by-products with a high boiling point and oligomers; unreacted reagents, the catalyst and polymerization inhibitors).

The invention is now described in greater detail and in a nonlimiting manner in the description which follows, with reference to FIGS. 1, 2 and 3 which illustrate schematically an apparatus which makes it possible to implement three embodiments of the process according to the invention.

DETAILED DESCRIPTION

One of the objectives of the invention is to use starting materials of natural and renewable origin, i.e. which are bio-based.

The 2-octanol used in the process according to the invention is an alcohol of renewable origin, in particular it can be obtained by alkaline treatment of ricinoleic acid derived from castor oil.

The acrylic acid used as starting material in the process according to the invention is essentially produced industrially from propylene.

However, independently of the use of the alcohol of renewable origin, the invention extends to the use, during the esterification, of acrylic acid of renewable origin, which may in particular be obtained from glycerol, according to a process comprising a first step of dehydration of the glycerol to give acrolein, followed by a step of gas-phase oxidation of the resulting acrolein; or obtained by dehydration of 2-hydroxypropionic acid (lactic acid) or 3-hydroxypropionic acid and of esters thereof.

The esterification reaction is carried out using the reagents in a 2-octanol/acrylic acid molar ratio which can range from 0.5 to 3, in particular between 1 and 1.5, at a temperature generally between 80° C. and 130° C., preferably between 90° C. and 120° C., at normal pressure or at reduced pressure, for example between 50 and 200 mbar and atmospheric pressure.

An acid esterification catalyst is used, generally an acid compound comprising sulfur, such as a sulfonic organic acid, for instance methanesulfonic acid, pare-toluenesulfonic acid, benzenesulfonic acid, dodecylsulfonic acid, xylenesulfonic acid, or mixtures thereof, or sulfuric acid. Methanesulfonic acid is preferably used as esterification catalyst. The catalyst is advantageously introduced in a proportion of from $5\times10^{-4}$ mol to $5\times10^{-2}$ mol per mole of 2-octanol.

The reaction is carried out in the presence of one or more polymerization inhibitors which are introduced into the reactor in a proportion of 500 to 5000 ppm relative to the crude reaction mixture. As polymerization inhibitors that can be used, mention may, for example, be made of phenothiazine, hydroquinone, hydroquinone monomethyl ether, di(tert-butyl)-para-cresol (BHT), para-phenylenediamine, TEMPO (2,2,6,6-tetramethyl-1-piperidinyloxy), di(tert-butyl)catechol, or TEMPO derivatives, such as OH-TEMPO, alone or mixtures thereof in any proportions. An additional addition of polymerization inhibitor is generally carried out at the level of the subsequent purification treatment.

Figure 1:
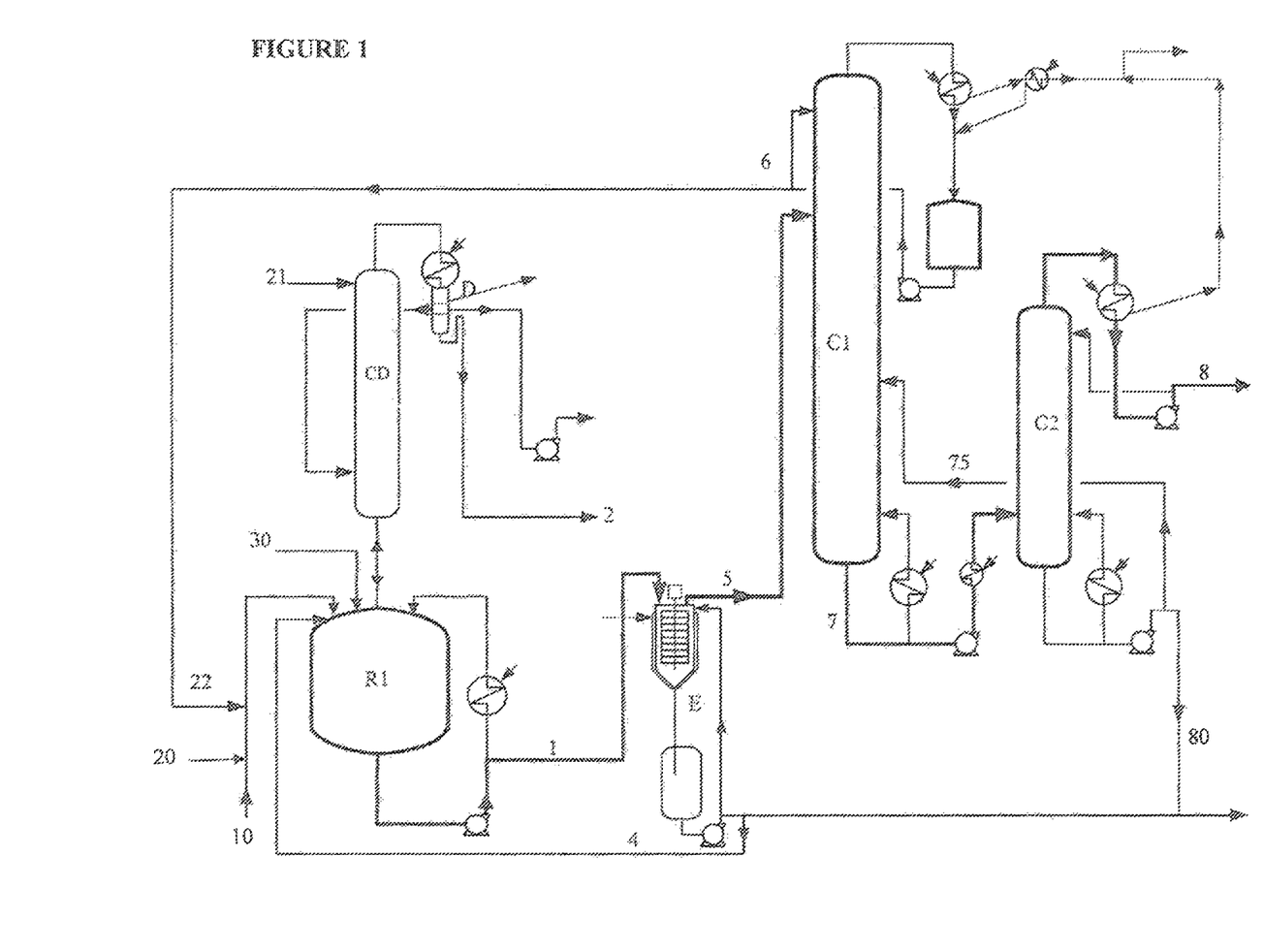
FIG. 1: illustrates a first embodiment, based on the prior separation of a stream rich in catalyst by means of a film evaporator, carried out on the reaction mixture, and then the purification of the 2-octyl acrylate using two distillation columns.
Figure 2:
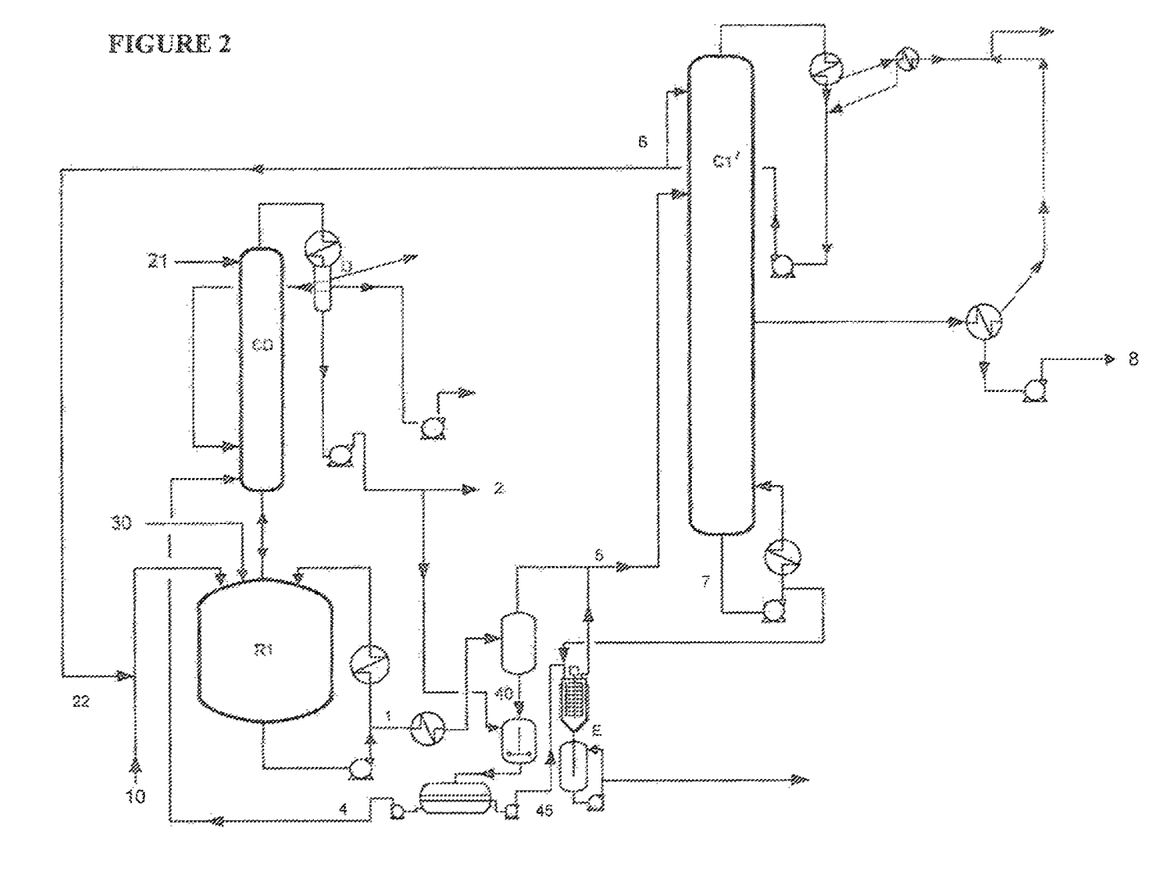
FIG. 2: illustrates a second embodiment which implements the separation of a stream rich in reaction product by partial evaporation of the reaction mixture, followed, on the one hand, by the purification of the reaction product by means of a distillation column and side take-off of the pure 2-octyl acrylate, and, on the other hand, by an extraction with water of the acid catalyst present in the residue of the reaction mixture and the recycling thereof to the reaction.
Figure 3:
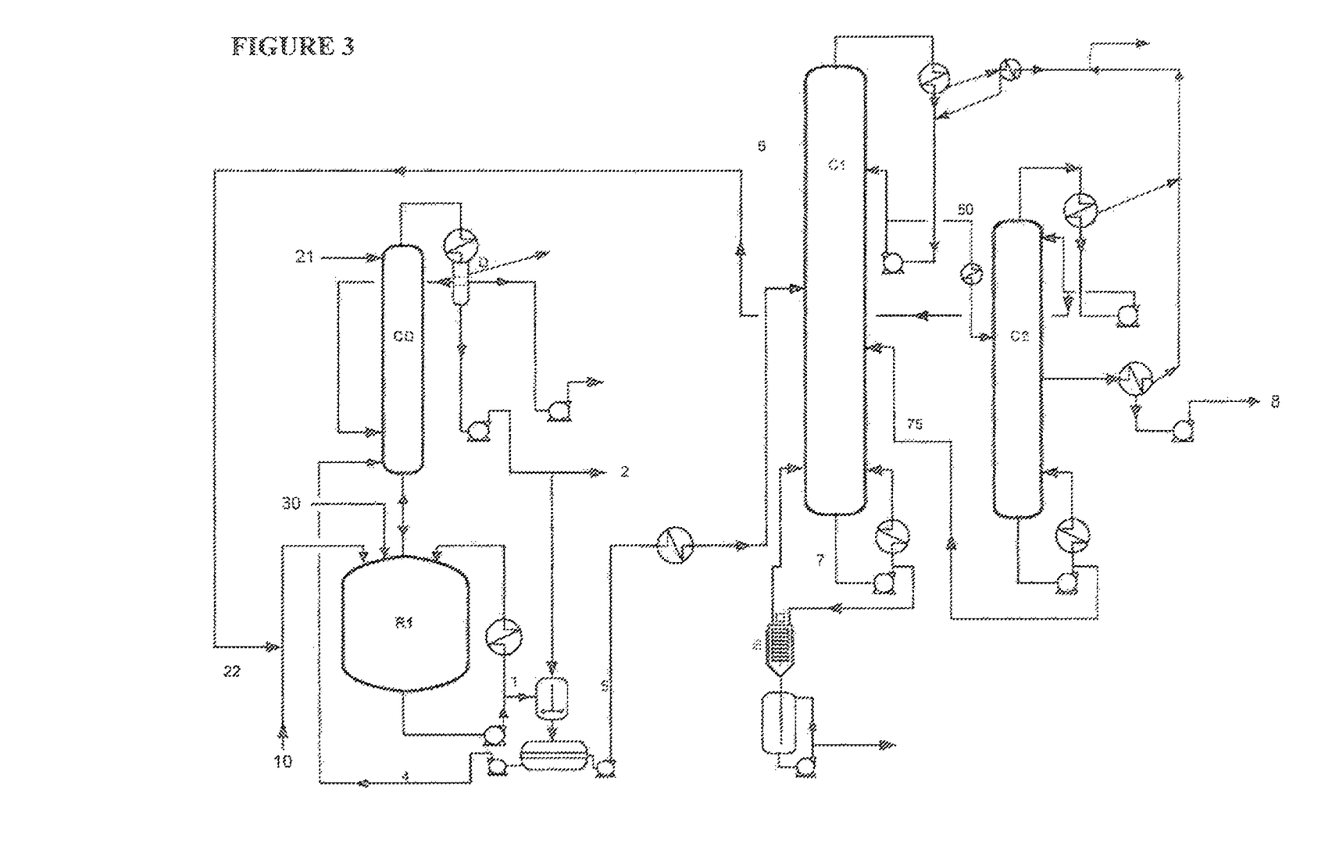
FIG. 3: illustrates a third embodiment, which implements an extraction with water of the catalyst present in the reaction mixture and the recycling thereof to the reaction, followed by the purification of the catalyst-free reaction mixture by means of two distillation columns with side take-off of the pure 2-octyl acrylate.

In accordance with the schemes represented in FIGS. 1, 2 and 3, the esterification reaction is carried out in a reactor R1 surmounted by a distillation column CD.

The reactor is a perfectly stirred reactor, heated by an external exchanger. It is surmounted by a stacked-packing distillation column CD or a plate distillation column CD comprising, for example, about ten theoretical plates. The assembly operates at a pressure of between 50 and 350 mbar and atmospheric pressure.

The acrylic acid is introduced directly into the reactor via the line 10 and the catalyst and the polymerization inhibitors are directly introduced into the reactor via the line 30. The 2-octanol is partly introduced directly into the reactor via the line 20 and partly at the top of the column CD via the line 21 so as to ensure reflux of the column. A recycled stream rich in 2-octanol originating from the subsequent purification steps can be introduced via the line 22.

During the reaction, a mixture containing predominantly the heteroazeotrope 2-octanol/water and a minor amount of acrylic acid is distilled, and separates, after condensation, into two phases in the decanter D. To this effect, the apparatus comprises a condenser fed with water at 25° C., and a decanter which receives the condensed heteroazeotrope, fitted with a system which makes it possible to optionally maintain a constant level of lower aqueous phase by automatically taking off the reaction water as it forms by virtue of the opening of a solenoid valve. A regulated vacuum system makes it possible to work under reduced pressure.

The upper organic phase 3 rich in 2-octanol and comprising a minor amount of acrylic acid is returned by overflow to the foot of the column CD.

The aqueous phase 2 is continuously taken off and is not reintroduced into the distillation column CD. The continuous taking off of this aqueous phase makes it possible to continually shift the equilibrium of the esterification reaction toward the formation of the 2-octyl acrylate and therefore to improve its selectivity.

According to one optional embodiment, the aqueous phase can be subjected to a distillation which makes it possible to recover the 2-octanol and the acrylic acid present in a low content, before its biological treatment and discharge.

After reaction with a residence time generally of between 2 and 5 hours, the reaction mixture 1 comprises between 60% and 90% by weight of reaction product (2-octyl acrylate), with unreacted 2-octanol and acrylic acid, the catalyst and the polymerization inhibitors, and also heavy by-products.

According to the invention, the reaction mixture is subjected to a purification treatment aimed at recovering the high-purity 2-octyl acrylate, and at recycling the exploitable products and avoiding discharge of pollutant streams, while at the same time minimizing the energy balance of the apparatus.

The purification treatment can be carried out according to different variants.

According to a first embodiment, illustrated in FIG. 1, the treatment for purification of the reaction mixture 1 comprises the following substeps:

- a first step of separation of the catalyst using a film evaporator E, at the end of which are separated, at the bottom, a stream 4 rich in catalyst and polymerization inhibitors, said stream 4 being at least partly recycled to the reaction, and, at the top, a stream 5 rich in 2-octyl acrylate; the stream 5 rich in 2-octyl acrylate is sent to a first distillation column C1 which makes it possible to recover, at the top, a stream 6 rich in 2-octanol which is recycled to the reaction and, at the bottom, a stream 7 rich in 2-octyl acrylate which is sent to a second distillation column C2 which makes it possible to separate, at the top 8, the pure 2-octyl acrylate and, at the bottom, a fraction containing heavy impurities and polymerization inhibitors which is either recycled to the first distillation column, or removed.

A falling film evaporator or a wiped film evaporator can in particular be used as film evaporator. This type of evaporator has the advantage of having a reduced residence time, thereby limiting the formation of additional heavy compounds downstream of the reaction section. This evaporator is composed essentially of a cylindrical part heated by a jacket, of an upper part which is used to separate the vapors and of a rotor rotating at high speed. The stream of reaction mixture to be treated is spread over the entire heating surface in the form of a film at high turbulence. The vapors which form rise in countercurrent manner toward the top of the apparatus. The nonevaporated products, essentially the catalyst and the polymerization inhibitors, reach the lower part of the evaporator and are evacuated in the form of a stream 4. The gas stream 5, at the top of the evaporator, constitutes the feed for the first column C1 of the purification sequence. The film evaporator operates under the operating conditions of the column C1.

The stream 4 containing virtually all the catalyst and the polymerization inhibitors is advantageously recycled to the reaction, preferably after flushing of the heavy impurities generated during the reaction, in particular the Michael adducts resulting from the addition of the 2-octanol to the 2-octyl acrylate, or the ester of the acrylic acid dimer.

The stream 5 rich in 2-octyl acrylate is sent to a first distillation column C1 so as to recover, at the top, a stream 6 rich in 2-octanol. The column C1 is generally a stacked-packing column or a plate column comprising about 15 theoretical plates, operating under reduced pressure, for example between 20 and 80 mbar, and it is heated by a thermosiphon or forced-recirculation external exchanger. At the top of this column C1, a polymerization inhibitor in solution in 2-octanol is generally introduced.

The stream 6 contains predominantly 2-octanol, but also residual acrylic acid and a small content of 2-octyl acrylate. It is advantageously recycled to the reaction via the line 22. The prior removal of the acid catalyst by means of the film evaporator minimizes the formation of octenes in this stream 6 during the distillation of the light compounds in the column C1.

The purification of the C1 column bottom stream 7, rich in 2-octyl acrylate, is continued by means of a second distillation column C2 which makes it possible to remove, at the bottom, the impurities still present and the polymerization inhibitors which are partly recycled, via the line 75, to the upper part of the column C1 or partly sent, via the line 80, to a treatment unit. The column C2 is a stacked-packing column or a plate column comprising about 5 to 10 theoretical plates, which operates for example at 10 mbar at the top of the column and is heated by a thermosiphon or forced-recirculation external exchanger. At the top of this column C2, a polymerization inhibitor in solution in 2-octyl acrylate is generally introduced.

The pure 2-octyl acrylate is recovered at the top of the column C2 (stream 8).

According to a second embodiment, illustrated in FIG. 2, the treatment for purification of the reaction mixture 1 comprises the following substeps:

- flash evaporation of the reaction mixture 1 resulting in the separation of a stream 5 rich in reaction product and of a reaction mixture residue 40;
- bringing, with stirring, the reaction mixture residue 40 into contact with water or an aqueous stream so as to form a two-phase system consisting of an aqueous phase 4 comprising the catalyst and an organic phase 45 rich in heavy by-products resulting from the reaction;

separation of said aqueous phase 4 and recycling thereof to the reaction:

separation of said organic phase 45 which is sent to a film evaporator E which makes it possible to separate a stream of exploitable products, such as reaction products and unreacted reagents, which is mixed with the stream 5;

sending the stream 5 rich in 2-octyl acrylate to a distillation column C1' which makes it possible to recover:

at the top, a stream 6 rich in 2-octanol which is recycled to the reaction, the pure 2-octyl acrylate via side take-off, and at the bottom, a stream 7 rich in heavy by-products and containing 2-octyl acrylate which is sent to the film evaporator E from which a fraction containing the heavy by-products and from which exploitable compounds have been removed, is removed.

According to this second embodiment, the acid catalyst is extracted from the reaction mixture from which most of the reaction product has been removed (stream 40).

The separation of the stream 5 rich in reaction product is carried out by means of a flash evaporation comprising the heating of the reaction mixture followed by an expansion at the operating pressure of the column C1' to which said stream 5 is sent. It is in particular possible to heat the reaction medium to a temperature of about 180° C. at a pressure of 3 bar, and then to perform an expansion at 65 mbar in a flash pot at a temperature of about 110° C.

The reaction mixture residue 40 is brought into contact and mixed in an extractor with water or an aqueous stream. Advantageously, the aqueous phase from the decanter D for separating the heteroazeotropic mixture generated by the reaction is used as aqueous extraction stream. The mixing is carried out by any mixing means at a mixing speed sufficient to allow the mass transfer required for the extraction of the acid compound from the residue, and the formation of an aqueous/organic two-phase system.

The aqueous phase separated by settling out 4, comprising most of the catalyst, is recycled to the reactor R1, or preferably to the bottom part of the column CD, after separation by settling out.

The organic phase 45, which may comprise exploitable products such as reaction products, polymerization inhibitors and residual reagents, is sent to a film evaporator E which makes it possible to recover a stream of exploitable products, which is mixed with the stream 5 before the purification carried out at the level of the column C1'.

The column C1' is generally a column comprising from 15 to 20 theoretical plates operating at 20 mmHg.

The column C1' operates as a tailing/topping column, i.e. makes it possible to separate, at the top, a stream 6 rich in light compound such as unreacted 2-octanol, and, at the bottom, a stream 7 rich in heavy by-products, said stream 7 being removed after passing over the film evaporator E.

The pure 2-octyl acrylate is recovered directly at the level of this column C1' via side take-off, in the liquid phase or in the gas phase, preferably in the gas phase, generally at an intermediate level located in the bottom part of the column, in particular between the theoretical plates 12 and 18.

This embodiment has the advantage of using just one distillation column C1'.

According to a third embodiment, illustrated in FIG. 3, the treatment for purification of the reaction mixture 1 comprises the following substeps:

bringing the reaction mixture 1 into contact with water or an aqueous stream so as to form a two-phase system consisting of an aqueous phase 4 comprising the catalyst, and of an organic phase 5 rich in reaction product;

separation of said aqueous phase 4 and recycling thereof to the reaction;

separation of said organic phase 5 which is sent to a first distillation column C1 which makes it possible to obtain:

at the top, a stream 50 rich in reaction product; and a at the bottom, a stream 7 rich in heavy by-products and containing 2-octyl acrylate, said stream 7 being sent to a film evaporator E from which a fraction containing the heavy by-products and from which the exploitable compounds recycled to the column C1 have been removed, is removed;

sending the stream 50 rich in reaction product to a second distillation column C2 which makes it possible to recover:

at the top, a stream 6 rich in 2-octanol which is recycled to the reaction;

the pure 2-octyl acrylate via a side take-off; and at the bottom, a stream rich in 2-octyl acrylate with polymerization inhibitors, which is at least partly recycled, via the line 75, to the column C1.

Like the second embodiment described above, the extraction of the catalyst with water directly on the reaction mixture minimizes the introduction of strong acid compound into the purification process and, consequently, the formation of octenes.

The reaction mixture from the reactor R1 is directly brought into contact and mixed in an extractor with water, or an aqueous stream. Advantageously, the aqueous phase from the decanter D for separating the heteroazeotropic mixture generated by the reaction is used as aqueous extraction stream. The mixing is carried out by any mixing means at a mixing speed sufficient to allow the mass transfer required for the extraction of the acid compound from the residue, and the formation of an aqueous/organic two-phase system.

The aqueous phase separated by settling out 4, comprising most of the catalyst, is recycled to the reactor R1, or preferably to the bottom part of the column CD, after separation by settling out.

The purification of the organic phase 5 is carried out using a first distillation column C1, operating as a tailing column (separation of the heavy by-products) and a second distillation column C2 operating as a topping column.

The columns C1 and C2 are, for example, columns comprising between 10 and 20 theoretical plates and operating at 20 mmHg at the top.

The operating of the column C2 makes it possible to obtain the pure 2-octyl acrylate at an intermediate level located in the bottom part of the column, in particular between the theoretical plates 12 and 18.

The process of the invention according to its different variants makes it possible to produce 2-octyl acrylate with a purity greater than 99.5%, or even greater than 99.8%.

The following examples illustrate the invention without limiting it.

Experimental Section

In the examples, the percentages are given by weight unless otherwise indicated, and the following abbreviations have been used:

AA: acrylic acid

2OCTA: 2-octyl acrylate

PTZ: phenothiazine

MSA: methanesulfonic acid

Example 1

According to the Invention, with Reference to the First Embodiment Illustrated by FIG. 1

2-Octanol, the MSA catalyst, the acrylic acid AA and the PTZ stabilizer are continuously introduced into the reactor R1, by means of a dip pipe. 2-Octanol is also introduced at the top of the distillation column CD which surmounts the reactor. These various constituents are in the weight proportions 63.9/1/35/0.1.

The esterification reaction is carried out under reduced pressure at 100 mbar at a temperature of 115° C., with a residence time of 3 h. During this step, the equilibrium of the reaction is shifted by taking off the water at the top of the column CD, in the form of a 2-octanol/water heteroazeotrope with a weight composition of 10/90 which is subjected, after condensation, to phase separation in a decanter D. The lower aqueous phase A, containing a small amount of 2-octanol, from this decanter is continuously taken off and removed after the 2-octanol has been recovered by means of a distillation column (not represented on the scheme). The supernatant organic phase O from the decanter D is continuously returned to the bottom of the column CD.

The reaction crude 1 at the outlet of the reactor R1 has the following weight composition:
2OCTA: 85.6%
2-Octanol: 11.3%
AA: 1%
PTZ+MSA: 2.1%.

The stream 1 from the reactor R1 is sent to a film evaporator E which separates, at the top, a stream 5 from which the MSA has been removed, and, at the bottom, a stream 4 containing predominantly the MSA catalyst and the PTZ stabilizer.

The stream 4 contains 2OCTA, 2-octanol, AA, and MSA with the stabilizer in the weight proportions 79.3/4/0.1/16.6. The majority of this stream 4 is recycled to the reaction, and the other minor part is sent to the treatment of the heavy compounds (not represented on the scheme).

The stream 5, from which the acid catalyst and the stabilizer have been removed, contains the 2OCTA, the 2-octanol and the AA in the weight proportions 86.9/12/1.1. This stream 5 is sent to a first distillation column C1 which separates, at the top, a stream 6 rich in unreacted alcohol and, at the bottom, a stream 7 containing predominantly the desired 2OCTA.

The stream 6 consists of 2-octanol, unconverted AA and 2OCTA in the weight composition 80.7/7.1/12.2. This stream 6 is recycled to the esterification reaction. The stream 7, at the bottom of the column C1, is sent to a second distillation column C2 which separates, at the top, the pure 2OCTA 8 having the composition:
2OCTA: 99.8%
AA: 100 ppm
2-octanol: 0.1%
other impurities: <0.1%
and, at the bottom, heavy compounds which are either sent to the heavy compound treatment station, or recycled to the upper part of the column C1.

Example 2

Comparative

The reaction crude 1 is sent directly to the distillation column C1. In this case, the presence of the acid catalyst promotes the formation of octenes in the column, and the stream 6 which leaves at the top of column C1 contains 10% of octenes. This stream can therefore not be recycled as it is to the reaction and requires an additional purification in order to remove the octenes.

The stream 7 at the bottom of the column C1 containing the 2OCTA, the MSA catalyst and the PTZ stabilizer is sent to the distillation column C2 so as to separate, at the top, the purified 2OCTA. In this case, the purity of the 2OCTA is only 98.5%. It contains 1% of octenes and 5000 ppm of 2-octanol. The 2-octyl acrylate obtained cannot be used as a monomer for manufacturing pressure adhesive polymers.

Example 3

According to the Invention, with Reference to the Second Embodiment Illustrated by FIG. 2

The stream 1 from the reactor R1 is preheated at 3 bar eff/180° C. in an exchanger, and is then expanded at 65 mbar abs/110° C. in a flash pot. The top stream 5 of the flash pot feeds the distillation column C1'. The flash bottom is mixed with all of the reaction water coming from the top of the column CD. After separation by settling out, an aqueous phase 4 consisting of water and MSA, which is recycled to the bottom part of the distillation column surmounting the reactor, and an organic phase 45 consisting of 2OCTA, unconverted reagents and heavy compounds and stabilizers, are recovered.

This stream feeds an evaporator E operating at 65 mbar abs/135° C. The heavy compounds leave at the bottom, and are sent outside the production unit for treatment, and a stream rich in 2OCTA, which is mixed with the stream 5 so as to feed the column C1', is recovered at the top.

The column C1' operates under a vacuum of 20 mmHg and comprises 17 theoretical plates. It separates, at the top, a stream 6 rich in 2-octanol, at the bottom, a stream 7 rich in 2OCTA and stabilizer, and at the side, the pure 2OCTA (stream 8).

Starting from a reaction mixture 1 having the composition:
2OCTA: 65%
2-octanol: 14%
AA: 9%
PTZ+MSA: 2%
the streams having the following compositions are obtained:
Stream 5:
2OCTA: 68.3%
2-octanol: 14.2%
AA: 9.2%
Stream 6:
2OCTA: 4.9%
2-octanol: 43.3%
AA: 28.1%.
This stream 6 can be recycled to the reaction.
Stream 8:
2OCTA: 99.8%
2-octanol: 0.1%
AA: 100 ppm
other impurities: <0.1%.
The stream 8 consists of the highly pure desired product.

Example 4

According to the Invention, with Reference to the Third Embodiment Illustrated by FIG. 3

The stream 1 from the reactor R1 is sent to a catalyst extraction section consisting of a mixer-decanter which operates at 80° C. In this section, the catalyst is extracted from the stream 1 by the aqueous phase A from the decanter D.

After separation by settling out, the following are recovered:
in the lower phase, an aqueous phase which contains between 25% and 30% of MSA and which is recycled to the reaction by being sent to the bottom part of the column CD.
in the upper phase, an organic phase 5 which now contains only 200 ppm of MSA and which has the following weight composition:
2OCTA: 86.5%
2-octanol: 11.8%
AA: 1.5%
PTZ+MSA: 0.2%.

This stream 5 is sent to a column C1 which separates, at the top, a mixture 50 having the composition:
2OCTA: 87%
2-octanol: 12%
AA: 1%
and, at the bottom, a mixture 7 rich in 2OCTA and heavy by-products which is sent to an evaporator E so as to recover, at the top, a stream containing predominantly 2OCTA and 2-octanol which is sent to the column C1, and, at the bottom, the heavy by-products which are removed.

The mixture 50 is sent to a column C2 which separates, at the top, a mixture 6 rich in 2-octanol and, at the bottom, a mixture rich in 2OCTA, part of which is recycled to the column C1 via the line 75.

The pure 2OCTA obtained by being taken off at the side of the column C2 has the following purity:
2OCTA: 99.8%
AA: 100 ppm
2-octanol: 0.1%
other impurities: <0.1%.

The invention claimed is:

1. A process for continuously producing 2-octyl acrylate, the process comprising the steps of (1) reacting acrylic acid and a branched secondary alcohol which is 2-octanol in the presence of a sulfuric acid esterification catalyst and at least one polymerization inhibitor in a reactor, (2) entraining water formed by the esterification reaction by distillation in a column surmounting the reactor in the form of a heteroazeotropic mixture with the 2-octanol which is condensed and then separated in a decanter to produce an upper organic phase and a lower aqueous phase, (3) purifying by separation a reaction mixture comprising reaction product and residual by-products to obtain, pure 2-octyl acrylate, unreacted 2-octanol, acrylic acid compounds, and catalyst, wherein said unreacted 2-octanol, acrylic acid compounds and catalyst are recyclable and wherein:
the aqueous phase derived from the decanter is continuously removed and not returned to the reactor;
the organic phase derived from the decanter is continuously recycled at the bottom of the distillation column surmounting the reactor; and
the treatment for purification of the reaction mixture comprises the steps of (i) separating a catalyst-rich stream which is at least partly recycled to the reaction step, (ii) separating a stream rich in unreacted 2-octanol which is at least partly recycled to the reaction step, and (iii) recovering pure 2-octyl acrylate.

2. The process as claimed in claim 1, wherein the treatment for purification of the reaction mixture comprises steps of:
first separating the catalyst using a film evaporator, at the end of which are separated, at the bottom, a stream rich in catalyst and polymerization inhibitors, said stream being at least partly recycled to the reaction, and, at the top, a stream rich in 2-octyl acrylate; and
second, sending the stream rich in 2-octyl acrylate to a first distillation column to recover, at the top, a stream rich in 2-octanol which is recycled to the reaction and, at the bottom, a stream rich in 2-octyl acrylate which is sent to a second distillation column to separate, at the top, the pure 2-octyl acrylate and, at the bottom, a fraction containing heavy impurities and polymerization inhibitors which is either recycled to the first distillation column, or removed.

3. The process as claimed in claim 1, wherein the treatment for purification of the reaction mixture comprises steps of:
flash evaporating the reaction mixture resulting in separation of a first stream rich in 2-octyl acrylate reaction product and of a reaction mixture residue;
bringing, with stirring, the reaction mixture residue into contact with water or an aqueous stream so as to form a two-phase system consisting of an aqueous phase comprising the catalyst, and an organic phase rich in heavy by-products resulting from the reaction;
separating said aqueous phase and recycling thereof to the reaction;
separating said organic phase which is sent to a film evaporator to separate a second stream of reaction products and unreacted reagents which is mixed with the first stream;
sending the first stream rich in 2-octyl acrylate to a distillation column to recover:
at the top, a third stream rich in 2-octanol which is recycled to the reaction,
pure 2-octyl acrylate via side take-off, and
at the bottom, a fourth stream rich in heavy by-products and containing 2-octyl acrylate which is sent to the film evaporator from which a fraction containing the heavy by-products is separated from reaction products and unreacted reagents and removed.

4. The process as claimed in claim 1, wherein the treatment for purification of the reaction mixture comprises steps of:
bringing the reaction mixture into contact with water or an aqueous stream so as to form a two-phase system consisting of an aqueous phase comprising the catalyst, and of an organic phase rich in reaction product;
separating said aqueous phase and recycling thereof to the reaction;
separating said organic phase which is sent to a first distillation column to obtain:
at the top, a stream rich in reaction product; and
at the bottom, a stream rich in heavy by-products and containing 2-octyl acrylate, said stream being sent to a film evaporator from which a fraction containing the heavy by-products is separated and removed from reaction products and unreacted reagents which are recycled to the first distillation column;
sending the stream rich in reaction product to a second distillation column to recover:
at the top, a stream rich in 2-octanol which is recycled to the reaction;
the pure 2-octyl acrylate via a side take-off; and
at the bottom, a stream rich in 2-octyl acrylate with polymerization inhibitors, which is at least partly recycled to the first distillation column.

5. The process of claim 1 wherein the catalyst is methanesulfonic acid.

6. The process of claim 1 wherein the reaction is carried out in a single reactor, the 2-octanol being introduced partly directly into the reactor and partly by means of the distillation column surmounting the reactor.

7. The process of claim 1 wherein the aqueous phase from the decanter is subjected to a distillation whereby any 2-octanol present is recovered before the aqueous phase is removed.

8. The process of claim 2 wherein the film evaporator is a falling film or wiped film evaporator operating under the conditions of the first distillation column.

9. The process of claim 1 wherein the acrylic acid is of renewable origin.

* * * * *